United States Patent [19]

Umemura et al.

[11] Patent Number: 5,158,071
[45] Date of Patent: Oct. 27, 1992

[54] ULTRASONIC APPARATUS FOR THERAPEUTICAL USE

[75] Inventors: Shinichiro Umemura; Nagahiko Yumita, both of Tokyo; Koshiro Umemura, Kanagawa; Kageyoshi Katakura, Tokyo, all of Japan

[73] Assignee: Hitachi, Ltd., Tokyo, Japan

[21] Appl. No.: 373,264

[22] Filed: Jun. 27, 1989

[30] Foreign Application Priority Data

Jul. 1, 1988 [JP] Japan .................................. 63-162512

[51] Int. Cl.⁵ .............................................. A61B 17/00
[52] U.S. Cl. ............................ 128/24 AA; 128/660.03
[58] Field of Search ..................... 128/24 AA, 660.03

[56] References Cited

U.S. PATENT DOCUMENTS

| | | | |
|---|---|---|---|
| 4,315,514 | 2/1982 | Drewes et al. | 128/660.03 X |
| 4,586,512 | 5/1986 | Do-hurr et al. | 128/660.03 |
| 4,622,972 | 11/1986 | Giebeler, Jr. | 128/24 AA |
| 4,646,756 | 3/1987 | Watnough et al. | 128/24 AA |
| 4,757,820 | 7/1988 | Itoh | 128/660.03 |
| 4,856,042 | 9/1989 | Umemura et al. | 128/660.03 |
| 4,893,624 | 1/1990 | Lele | 128/24 AA |
| 4,913,156 | 4/1990 | Inbar et al. | 128/24 EL |
| 5,040,537 | 8/1991 | Kotohura | 128/24 AA |

Primary Examiner—Francis Jaworski
Attorney, Agent, or Firm—Antonelli, Terry Stout & Kraus

[57] ABSTRACT

An ultrasonic apparatus for thereapeutical use, especially for remedying a malignant tumor, through activation of a drug at a desired local portion inside of a living body by sequentially irradiating a plurality kinds of convergent ultrasonic waves having different focal positions of different acoustic pressure distribution shapes but having a mutually overlapping focal zone and by switching them within a short period. The drug is activated as a promotor for an ultrasonic therapeutical effect through continuous generation and rupture of cavitation caused by the irradiated and switched ultrasonic waves.

3 Claims, 13 Drawing Sheets

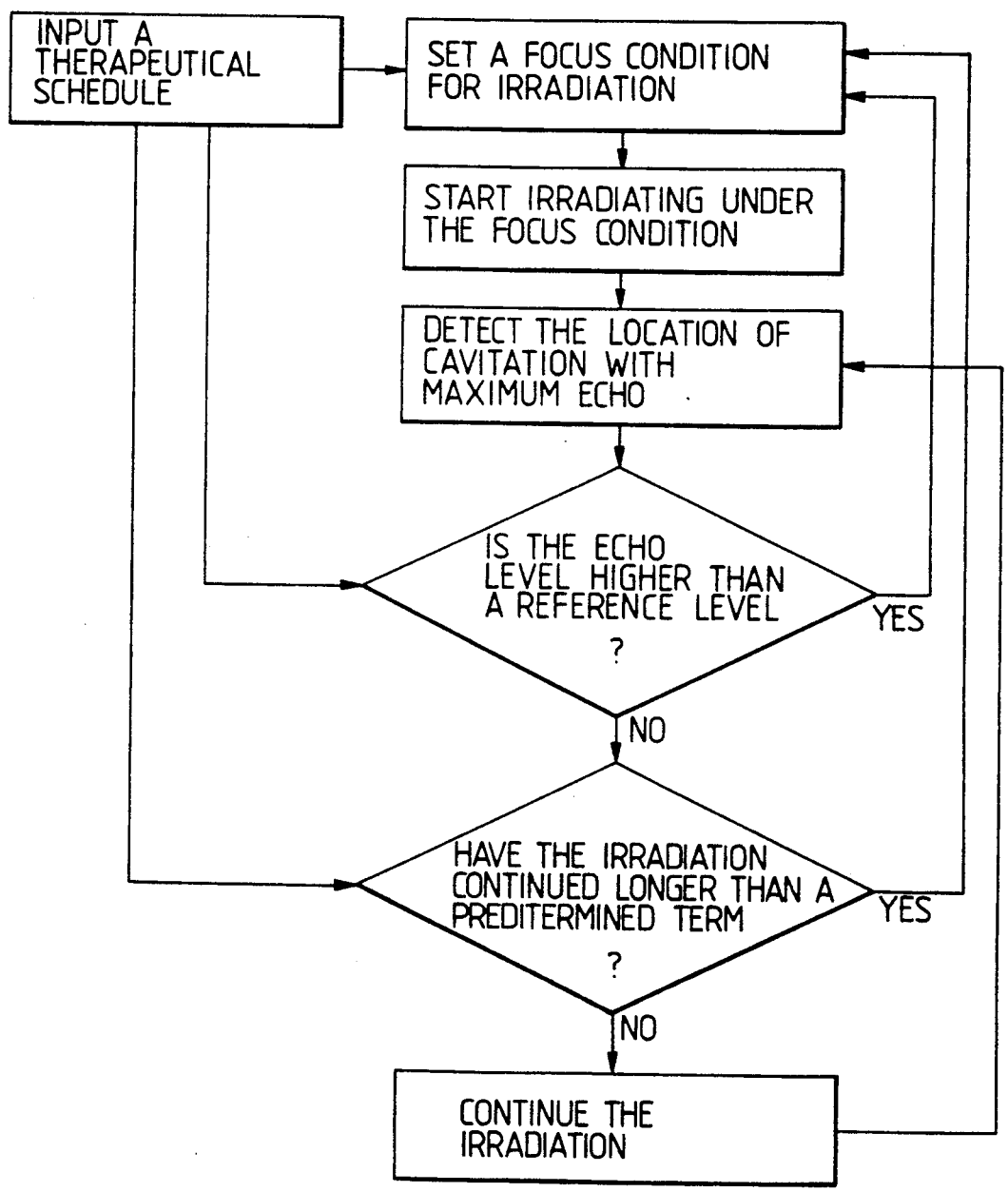

ULTRASONIC APPARATUS FOR THERAPEUTICAL USE

BACKGROUND OF THE INVENTION

1. Field of the Invention

This invention relates to a ultrasonic apparatus for therapeutical use for remedying a malignant tumor or the like, to a ultrasonic apparatus for litholysis by utilizing drug activation by a ultrasonic wave or to a ultrasonic apparatus for promoting a chemical reaction.

2. Description of the Prior Art

A prior art technique of activating a drug at only an affected part by irradiation of a ultrasonic wave and remedying selectively the affected part by restricting side effects on the whole body is described in a research article in "Japanese Journal of Hyperthermic Oncology", Vol. 3[2] (1987), pp. 175-182. This prior art reference describes the anti-cancer effect due to the synergistic effect of drug dose and a non-thermal action of a ultrasonic wave on the cancer tissue which is artificially transplanted and multiplied near the body surface of an experimental small animal. A heretofore known anti-cancer drug such as adriamycin or daunomycin is used as the anticancer drug and ultrasonic wave irradiation means is the one that can generate a plane wave having an expansion somewhat greater than the diameter of the tumor to be treated. The paper reports that the decrease in the tumor diameter and the extension of life after the treatment were significant for the group to which the ultrasonic wave was irradiated after the administration of the anticancer drug in comparison with the group to which only the anticancer drug was dosed and with the group to which only the ultrasonic wave was irradiated.

SUMMARY OF THE INVENTION

The prior art technique described above involves the problem in that it is not effective for the remedy of a deep tumor because it uses the plane wave. Moreover, since the effect of local activation of the drug by the irradiation of the ultrasonic wave is not sufficient, the kind and amount of the drug used might give the side effect on the normal tissue, too.

It is therefore an object of the present invention to provide a ultrasonic apparatus for therapeutical use capable of effectively remedying not only a tumor on the surface but also a deep-seated tumor.

It is another object of the present invention to provide a ultrasonic apparatus for therapeutical use having a high effect of locally activating a drug at an intended portion and therefore having an extremely low side effect on the normal tissue other than the intended portion.

It is still another object of the present invention to provide a ultrasonic apparatus for therapeutical use capable of letting a drug, which does not have an anti-cancer effect by itself or has an extremely low anticancer effect and hence has an extremely low side effect, exhibit a local anticancer effect in the human body, and also to provide a drug to be used in such a therapeutical apparatus.

Utilization of cavitation is effective for the activation of a drug by a ultrasonic wave and such an activation action can be obtained particularly at the time of rupture of cavitation. On the basis of this concept, the ultrasonic apparatus of the present invention causes efficiently the generation and rupture of the cavitation in a selected region of the body by use of a convergent ultrasonic wave. More definitely, the present invention provides a ultrasonic wave irradiation apparatus for causing the generation and rupture of cavitation by irradiating interruptedly a convergent ultrasonic wave with a suitable time interval or by irradiating a ultrasonic wave while changing over within a short period a plurality of kinds of convergent acoustic fields having mutually overlapping focal zones, though their focal points or acoustic wave distribution shapes are different.

When a convergent ultrasonic wave having high intensity and long wave train is irradiated to a living body or to water in which a gas exists in elution, cavitation takes place near the focal point. When this cavitation is ruptured, the efficacy of the drug existing in elution near the cavitation is activated. However, the formation and rupture of the cavitation is not effected efficiently by the irradiation of a ultrasonic wave continuous for a long period, and efficacy activation can be made more efficiently by the repetition of irradiation of a burst wave having a predetermined duration time. The accurate position at which cavitation is more likely to be generated among the positions near the focal point is in agreement with the maximum acoustic pressure position so long as its size is very small but when cavitation grows to the size such as the one that can be detected by a ultrasonic echo of a frequency substantially equal to the irradiated ultrasonic wave, the accurate position moves close to the minimum acoustic pressure position. Accordingly, efficiency of the formation and rupture of cavitation can be improved further by irradiating sequentially or alternately a plurality of kinds of convergent ultrasonic waves which, though their focal zones overlap with one another, have mutually different acoustic pressure distribution shapes or more definitely, have mutually different maximum acoustic pressure positions, while changing them over within a short period.

The present invention proposes a ultrasonic therapeutical effect promoter consisting, as a principal agent, of a compound which does not have the anticancer effect by itself or has a very low effect, but exhibits a remarkable anticancer effect when activated by the irradiation of a ultrasonic wave, and its derivatives, such as chelation formation compounds represented by porphyrin compounds and alkylating agents, and ascorbicssalts. Such drugs do not at all have any side effect on the normal tissue not irradiated with the ultrasonic wave or their side effect, and even when it exists, they can be used so that the side effect can be neglected substantially. Accordingly, they are extremely suitable for the calcinomatic therapy by the application of the ultrasonic wave irradiation as the object of the present invention.

BRIEF DESCRIPTION OF THE DRAWINGS

FIG. 9 is a flowchart showing an example of the algorithm of a series of operations such as setting of a focus condition for irradiation, detection of stable cavitation, change of the focus for irradiation, and the like.

DESCRIPTION OF THE PREFERRED EMBODIMENTS

Hereinafter, preferred embodiments of the present invention will be described with reference to FIGS. 1 to 16.

Figure 1A:
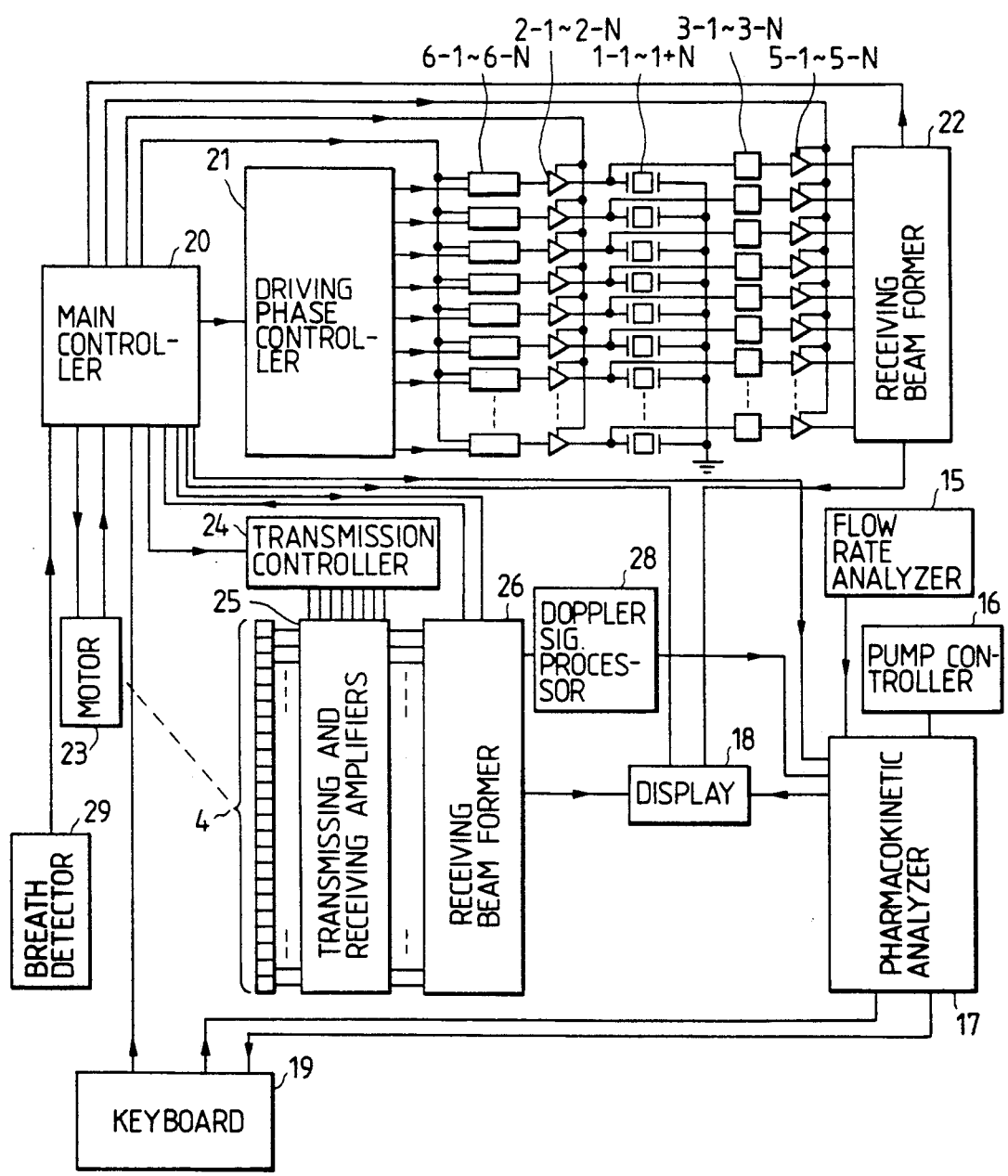
FIG. 1(A) is an overall structural block view of a ultrasonic apparatus for therapeutical use having the support function of a drug dosage and ultrasonic wave irradiation in accordance with one embodiment of the present invention.
Figure 1B:
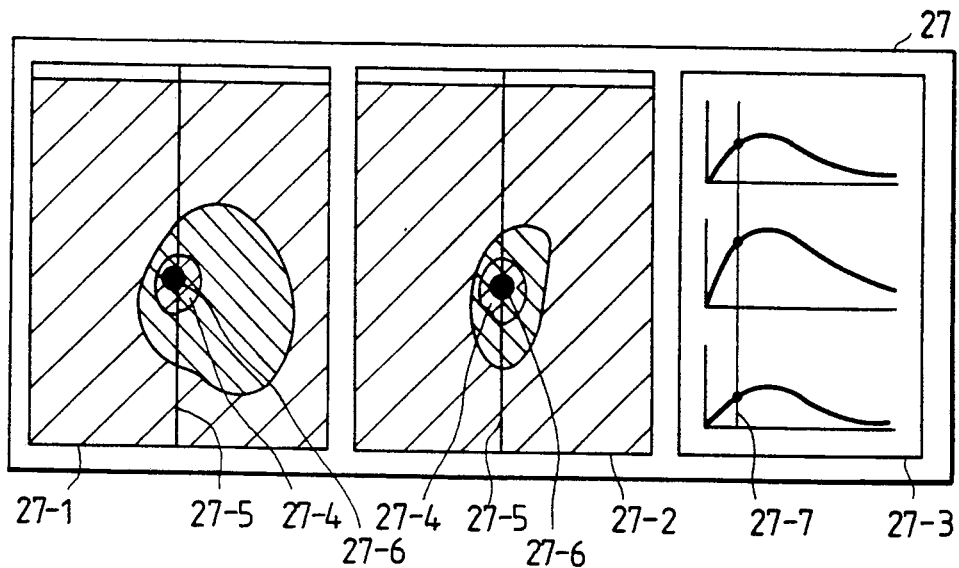
FIG. 1(B) is a schematic view showing a display surface of FIG. 1(A)
Figure 3:
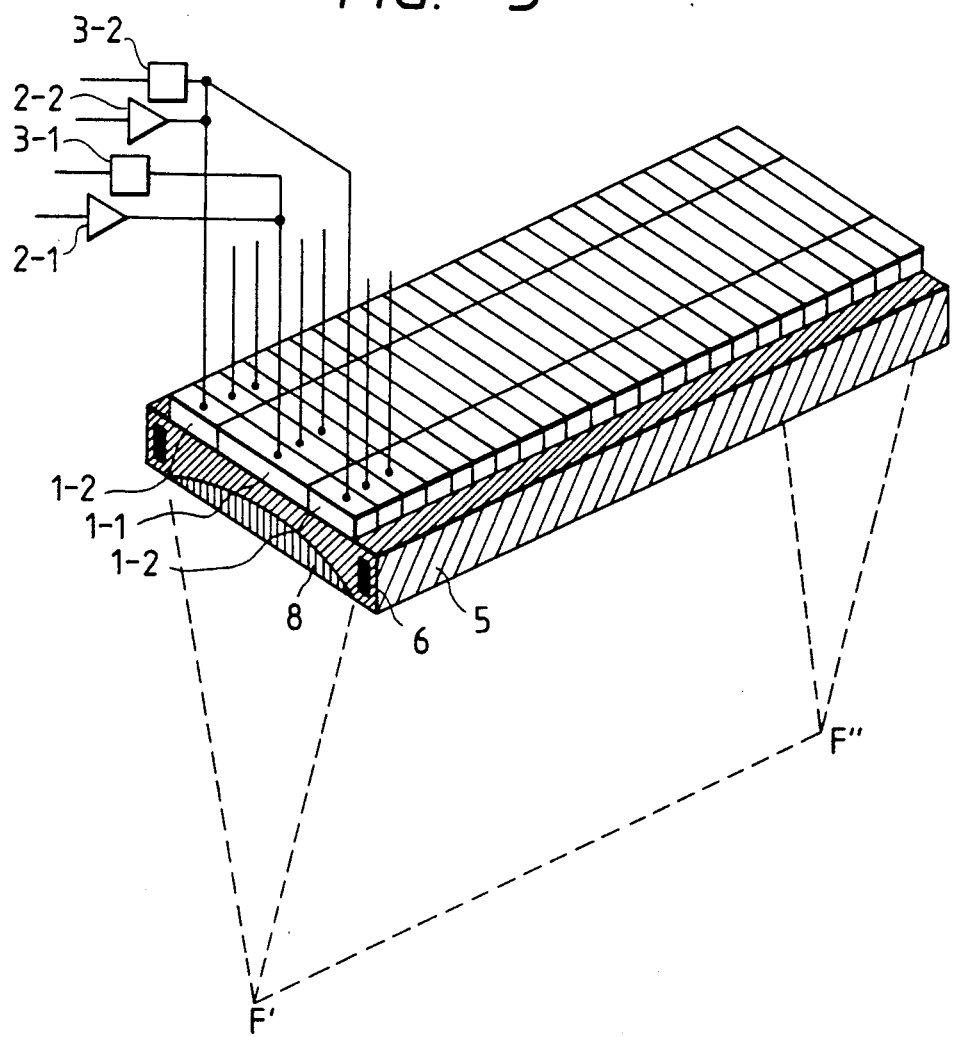
FIGS. 2(A), 2(B) and 3 show the structures of a ultrasonic wave applicator, respectively.
Figure 4:
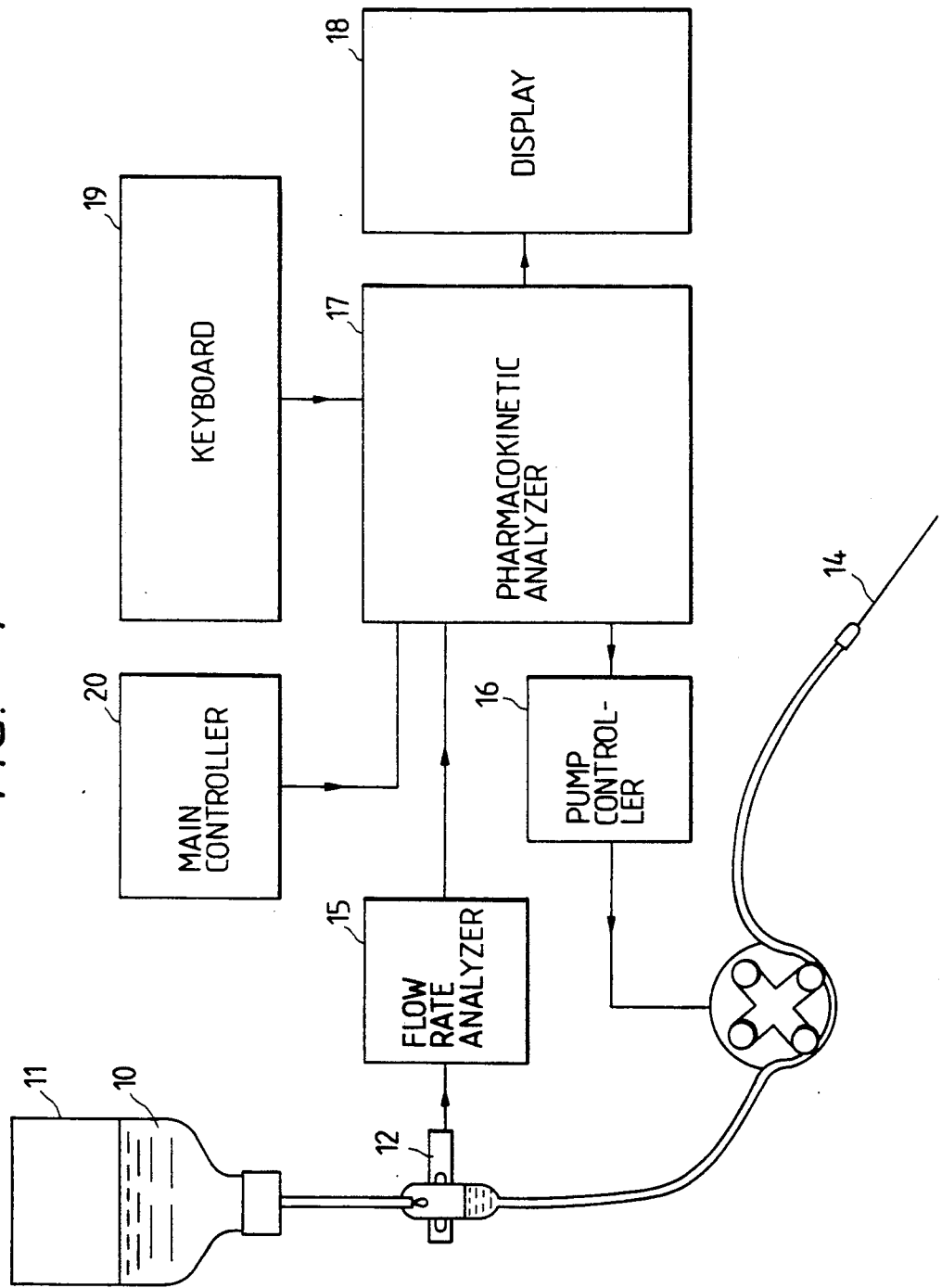
FIG. 4 shows an example of a drug dose portion.

The overall construction of a ultrasonic apparatus for therapeutical use in accordance with one embodiment of the present invention, which has the function of supporting the cooperation between the dose of a drug and the irradiation of a ultrasonic wave, is shown in FIG. 1(A), an example of the display of this apparatus is shown in FIG. 1(B), the structure of a ultrasonic wave applicator is shown in FIGS. 2 and 3 and the structure of a drug dose support portion is shown in FIG. 4.

In FIG. 1(A), the information on the ultrasound irradiation therapeutical schedule is inputted from a keyboard 19 to a main controller 20 and an irradiation focus code signal which determines the focal zone position and sound pressure distribution shape of the irradiating field on the basis of the information is given from the main controller 20 to a driving phase controller 21. The driving phase controller 21 designates the phase of the driving signals generated from driving signal generators 6-1-6-N (where N is the total number of transducer independent elements) in accordance with the code signal given thereto. Each driving signal thus generated is power-amplified by each driver 2-1-2-N and is applied to each transducer element 1-1-1-N so that a ultrasonic wave converged to a desired portion is irradiated. A signal given directly from the main controller 20 controls the generation and stop of the driving signal of each driver 2-1-2-N so that the duration time of the irradiated ultrasonic wave can be controlled and the intensity can be changed without changing the irradiation focus and emergency stop of the ultrasound irradiation can be made when any abnormality occurs.

Each transducer for irradiation operates also as a reception transducer for detecting cavitation occurring in the object of the irradiation. After the component of an irradiation signal band is removed from the signal received by each transducer element 1-1-1-N by each band-pass filter 3-1-3-N, the signal is led to each receiving amplifier 5-1-5-N and amplified there. Thereafter, the signal is applied to a receiving beam former 22. A series inductance resonating with the sum of an element capacity and a cable capacity at a driving frequency $f_o$ is inserted into the output portion of each driver 2-1-2-N. Therefore, there is not a high possibility that the output impedance of the driver serves as a shunt and remarkably lowers reception sensitivity. Each receiving amplifier 5-1-5-N has a variable gain and this gain is controlled by the signal given directly from the main controller 20. This gain is lowered to avoid saturation of the amplifier in the time zone where great quantities of unnecessary signal components other than the center frequency of the irradiated ultrasonic wave occurs, such as at the time of change-over of the irradiation focus. A receiving beam former 22 has a plurality of focus circuits converging to a plurality of focuses arranged with gaps therebetween that correspond to the spatial resolution of a reception system inside the irradiation focal zone, detects the occurrence and occurrence positions of subharmonic components such as $f_o/2$ and $f_o/3$ that are emitted by the cavitation and higher harmonic components and provides the detection signal to the display 18.

FIG. 1(B) shows the display surface in the display and the cavitation occurrence position detected as described above is displayed as represented by reference numeral 27-6 on the display surface 27. The information on the position and size of the cavitation is applied to the irradiation main controller 20 and when the cavitation is judged to be greater than a predetermined standard, the irradiation focus is switched and the maximum of the sound pressure is moved to that position. The production cost of the receiving beam former 22 can be reduced by use of a smaller number of parallel processing focus circuits so as to scan their respective focuses in the irradiation focal zone.

In FIG. 1(A), reference numeral 4 represents an array type ultrasonic probe for imaging and reference numeral 23 is a motor which rotates the probe around the axis perpendicular to the probe surface, and obtains a plurality of ultrasonic echo tomograms 27-1 and 27-2 necessary for locating the irradiation target. Each element of the probe 4 is connected to the transmission controller 24 and to the receiving beam former 26 through the transmitting and receiving amplifier 25. The echo tomograms thus obtained are displayed as represented by 27-1 and 27-2 in FIG. 1(B). In other words, an irradiation focal zone mark 27-4, intersection 27-5 of sectional planes of a plurality of tomograms and a cavitation detection position mark 27-6 are superposed and displayed in mutually distinguishable colors on the display surface 27 under the control of the display 18. To obtain good imaging resolution, the ultrasonic wave frequency band of the probe 4 is at least 2 $f_o$. The higher harmonic components such as 2 $f_o$, 3 $f_o$, etc., that are emitted by the cavitation may be detected by the probe 4.

If the motion of the object portion due to breathing cannot be neglected and becomes a problem through the examination of the object region by the echo tomograms 27-1 and 27-2, the irradiation focus is controlled to move in such a manner as to follow up the motion of the object portion on the basis of the signal that is applied from the receiving beam former 26 to the irradiation main controller 20. If the motion of the object portion is so great that it exceeds the range where the irradiation focusing is possible or tracking becomes difficult, the ultrasonic wave irradiation timing is synchronized with the aspiration on the basis of the signal given from a breath detector 29 to the main controller 20 so that the ultrasonic irradiation can be made within a certain predetermined range of the aspiration time phase.

Reference numerals 15 to 17 in FIG. 1(A) represents a mechanism for supporting the cooperation between the drug dose and the ultrasonic wave irradiation. This portion is shown more definitely in FIG. 4. A dip drug 10 whose anti-tumor effect is activated by the ultrasonic wave irradiation is placed into a transparent container 11 and is communicated with a needle 14 through a flexible tube. In connection with the drug flow rate, the output from an optical drop counter 12 is inputted to a flow rate analyzer 15 and the flow rate per unit time is inputted to a pharmacokinetic analyzer 17. The information such as the name of the drip drug, the dose method, the name, weight, length, age and blood protein concentration of a patient, the name and portion of the remedial object, the kind of tumor, and the like, are inputted from the keyboard 19 into the pharmacokinetic analyzer 17. In addition to the dose drug information described above, the dose time of the drug, that has been dosed before the start of instillation, is also inputted from the keyboard 19 into the pharmacokinetic analyzer 17. On the basis of these input information, the pharmacokinetic analyzer 17 estimates the past, present and future drug concentrations of the object region and those of the portions nearby through numeric calculation on the basis of the pharmacokinetical aspect and provides the estimation values to the display 18, which displays the result on the display surface 27 such as 27-3 of FIG. 1(B). A present time marker 27-7 is displayed, too, on the graph displayed. A "pharmacokinetical ultrasonic dose" is calculated from both the internal drug concentration and the ultrasonic wave dose at each portion in the body and is also displayed on the display surface 27. If the difference between the estimated value of the interior drug concentration and the scheduled value for the therapeutical plan is automatically judged to be greater than a preset value, the pressure-feed quantity of a drug pump 13 is controlled through a pump controller 16 to bring it closer to the scheduled value.

Turning back again to FIG. 1(A), the keyboard 19 is equipped with recording means such as a magnetic or optical disc or an IC card, records the pharmacokinetical ultrasonic dose in addition to the various information on the patient and the drug dose method and uses them as the recorded information for the future diagnosis and remedy of the patient.

When the number of blood vessels flowing out from and into the organ as the object of irradiation is not much great, the focuses of the transmission controller 24 and the receiving beam former 26 are brought into conformity with the blood vessels and the output of the receiving beam former 26 is processed by a Doppler signal processor 28 in order to determine the blood flow velocity and the estimated value of the blood flow rate per unit time of the object organ from the diameter of the blood vessel as well as its change with time. These data are given to the pharmacokinetic analyzer 17. Using these data, the pharmacokinetic analyzer 17 corrects the drug concentration estimated value in the object organ. If it is difficult to measure the blood flow rate of the object organ itself, the change with time of the blood flow rate of the more whole body such as that of the main artery of the abdominal region and the result is given to the pharmacokinetic analyzer 17 to correct the estimated drug concentration.

Hematoporphyrin which is likely to cause the photochemical reaction is often used as the drip drug 10 shown in FIG. 4. Therefore, the light source used for the optical drop counter 12 must have the minimum necessary intensity. A shield cover is put to the transparent container 11, whenever necessary, to prevent the change with time of the drug due to light.

Figure 2A:
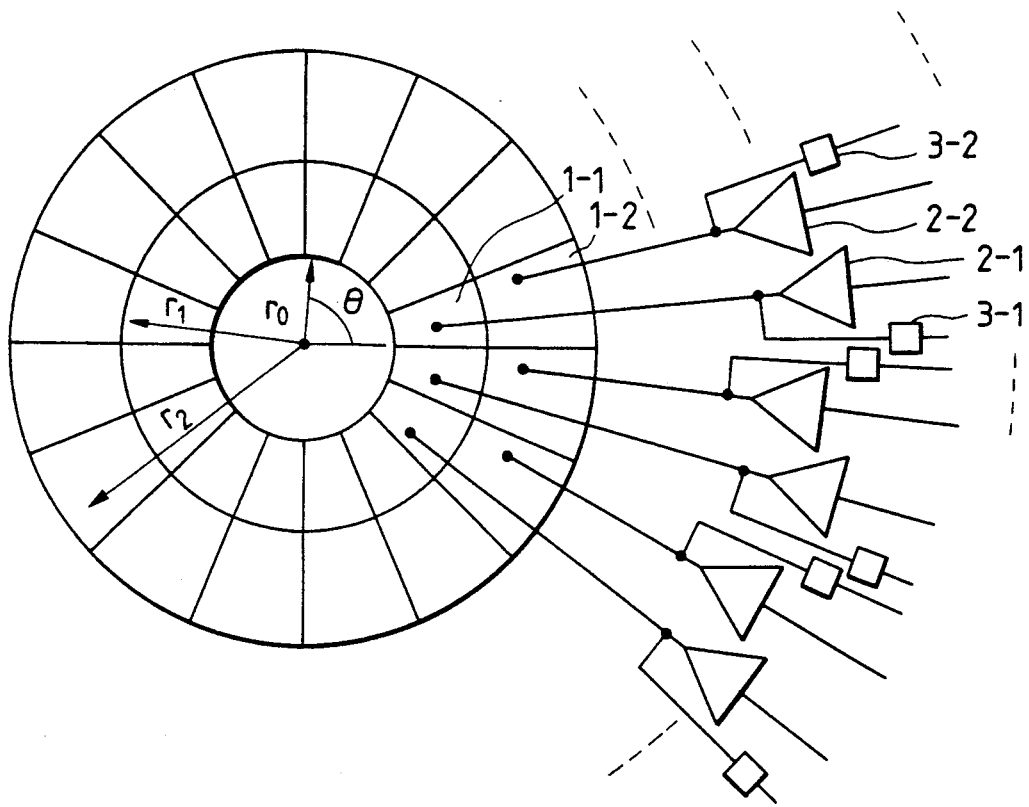
Figure 2B:
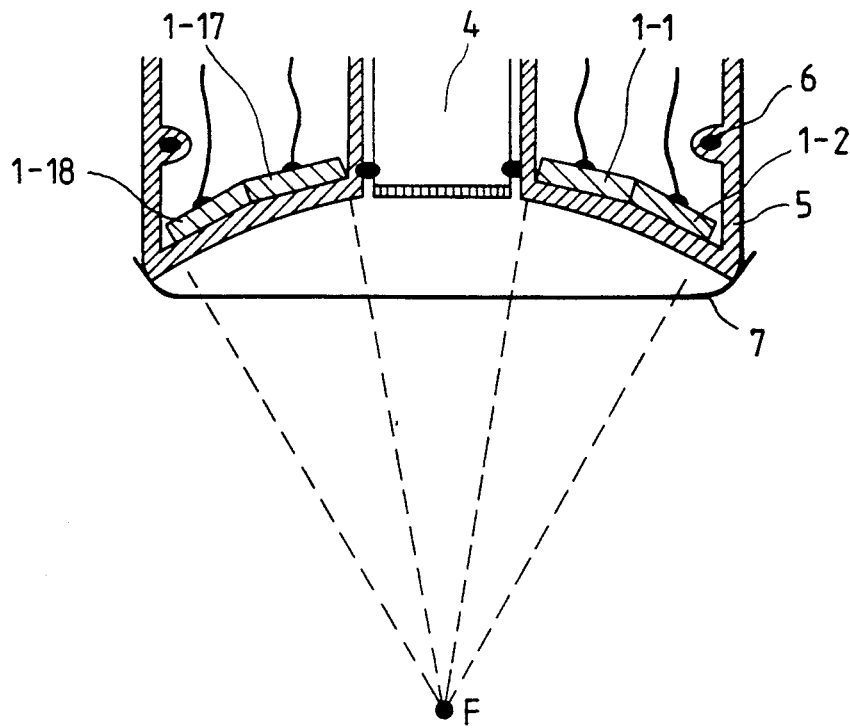

Referring to FIGS. 2(A) and 2(B), the ultrasonic applicator of this embodiment will be explained in further detail. FIG. 2 shows an example of 16-sector 2-track array type applicator having a geometric focus F by way of example, FIG. 2(A) is its plane view and FIG. 2(B) is its sectional view.

As can be seen from FIG. 2(A), the ultrasonic irradiation transducer elements represented by reference numerals 1-1, 1-2 and the like are arranged in a double circle. A piezoelectric ceramic of a lead titanium type is used as the electro-optical conversion material of this element. As shown in FIG. 2(B), each element is bonded to an acoustic matching layer 5 made of a light metal consisting principally of magnesium by use of an epoxy type specific adhesive having a small coefficient of thermal expansion as the polymer. Besides the materials described above, it is possible to use the piezoelectric ceramics of the lead zirconate type, the lead titanate type or the light metal consisting of aluminum. Since the element has the acoustic matching layer, the frequency range of the ultrasonic wave that can be irradiated becomes wider than when there is no acoustic matching layer and is from 0.5 to 1 MHz. Though sensitivity somewhat drops, reception of the ultrasonic wave in a broader frequency range becomes possible. The matching layer 5 describes a concave forming a part of the spherical plane with the geometric focus F on the ultrasonic wave irradiation plane side being its center, and its pack is a polished polyhedron for bonding thereto the piezoelectric ceramic element. This light metal acoustic matching layer 5 has good thermal conductivity and is therefore effective for cooling the piezoelectric ceramic element at the time of irradiation of the ultrasonic wave. It also operates as a ground electrode of each piezoelectric element. The matching layer 5 forms a part of the applicator housing. A coolant fluid passage 6 is disposed so as to absorb the heat generated at the time of irradiation of the ultrasonic wave and a water bag 7 storing therein deaerated water is fitted so as to facilitate acoustic coupling with the body surface.

The array type ultrasonic probe for imaging 4 is stored in the round hole at the array center. The probe structure is the same as the one that is used for a ultrasonic diagnostical apparatus and the ultrasonic wave frequency used in this embodiment is from 2 to 4 MHz. The probe 4 is rotated round the center axis of the applicator with respect to the applicator housing 5 so that a plurality of tomograms can be obtained by a single unidirectional array probe, and this rotation is caused by the motor 23.

In this embodiment, the geometric focal length of the applicator is 12 cm, the outer diameter $2r_2$ is 12 cm, its inner diameter $2r_0$ is 4 cm and the diameter $2r_1$ of the circle dividing these two tracks is 8 cm.

The acoustic field generation method of the present invention will be described in detail hereafter by setting the polar coordinates $(r, \theta)$ on the array plane, the angular coordinates at the center of the nth element to $\theta_n$ and the driving signal of the nth element of the ith track to $A_i(\theta_n)$.

Figure 5A:
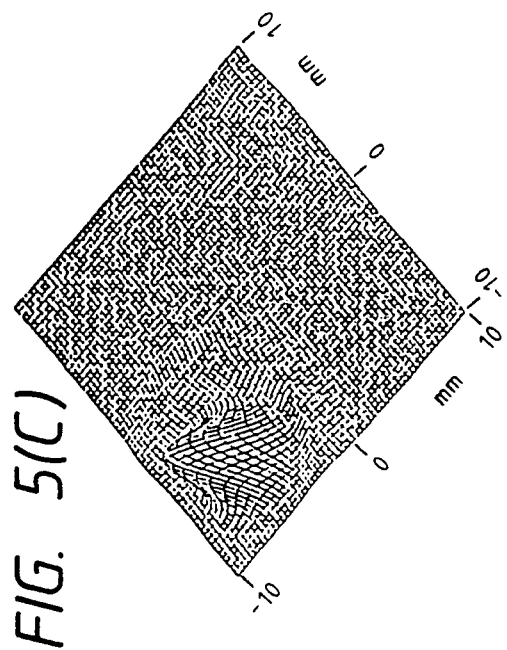
FIGS. 5A, 5B, 5C, 5D, 6A, 6B, 10A, 10B, 11A and 11B are bird's-eye views of the field intensity distribution formed on the geometric focus by the applicators of FIGS. 2(A) and 2(B) in the embodiment of the present invention, respectively.
Figure 5C:
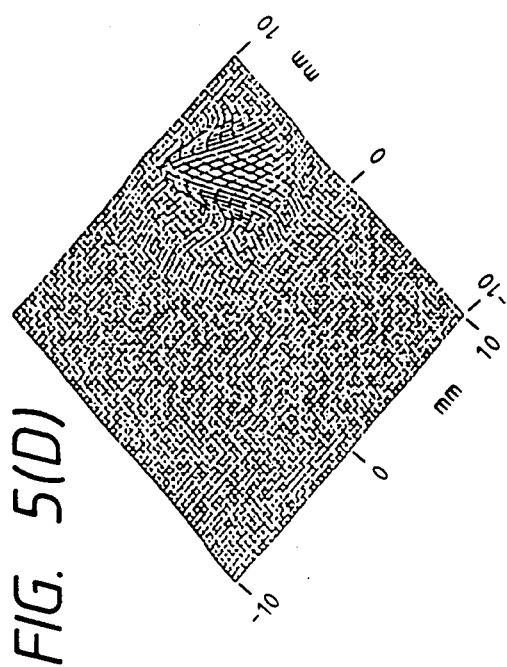
Figure 5B:
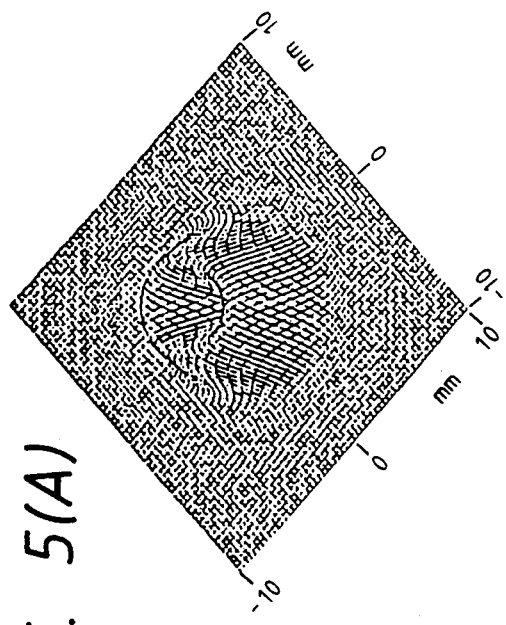

When each element is driven by a driving signal whose phase rotates M times round the periphery of the array:

$$A_1(\theta) = A_o \exp j(M\theta - \omega t) \quad (1)$$

an acoustic a field which is approximated by use of an M- th order Bessel function is formed on the geometric focal plane. If the ultrasonic wave frequency is 0.5 MHz and M=1, for example, the intensity distribution of the acoustic field formed on the geometric focal plane is shown in FIG. 5A. When the ultrasonic wave is irradiated for a while to water eluting therein a gas or to the living body by use of the field shown in FIG. 5A, a cavitation is formed and grows near the sound pressure minimum point encompassed by the sound pressure maximum portion and gets stable. At this point of time, the irradiation of the ultrasonic wave is switched and made within a short period to the acoustic field having the acoustic pressure maximum point at the position of the acoustic pressure minimum point such as shown in FIG. 5B, the stable cavitation is broken and insteads, a large number of fine cavitations repeat for a while the formation and rupture which are useful for the activation of the drug near the acoustic pressure maximum point. In FIG. 5B, the driving signal having the same phase for all the elements, that is, the signal whose M=0 in the formula (1), is applied to drive all the elements so as to form the focus of the irradiation field at the position of the geometric focus F.

Figure 6A:
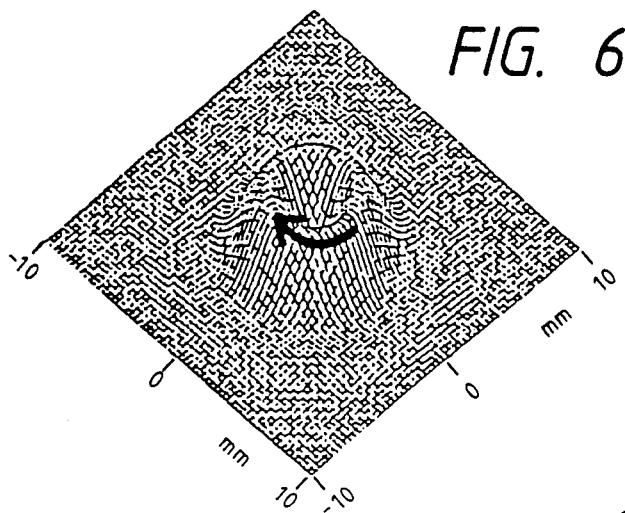
Figure 6B:
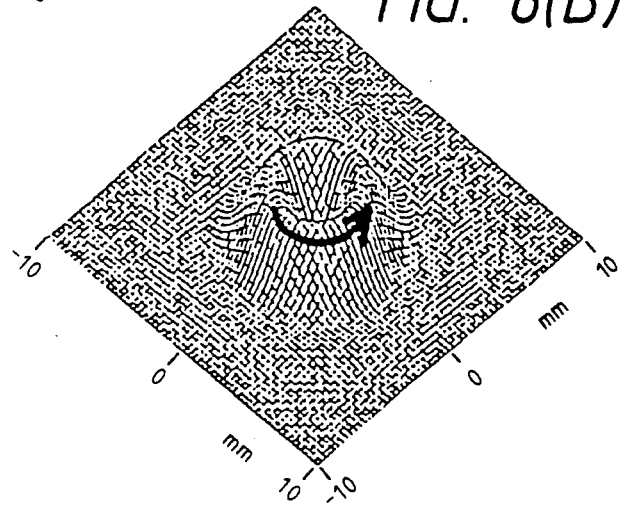

The acoustic field in which the ultrasonic wave power distribution is approximated by the same M- th order Bessel function is two fold: one having a positive M and the other, a negative M. The rotating directions of their wave planes are mutually different as shown in FIGS. 6(A) and 6(B). This acoustic field will be hereinafter referred to as a "conjugate acoustic field". This conjugate acoustic field has different positions of points at which the cavitation gets stable because the inclinations of the wave planes are different, even though the ultrasound power distribution is the same, in a heterogeneous medium such as in the living body. Therefore, the formation and rupture can be conducted extremely efficiently by the irradiation of the ultrasonic wave using alternately the conjugate acoustic fields.

Figure 7:
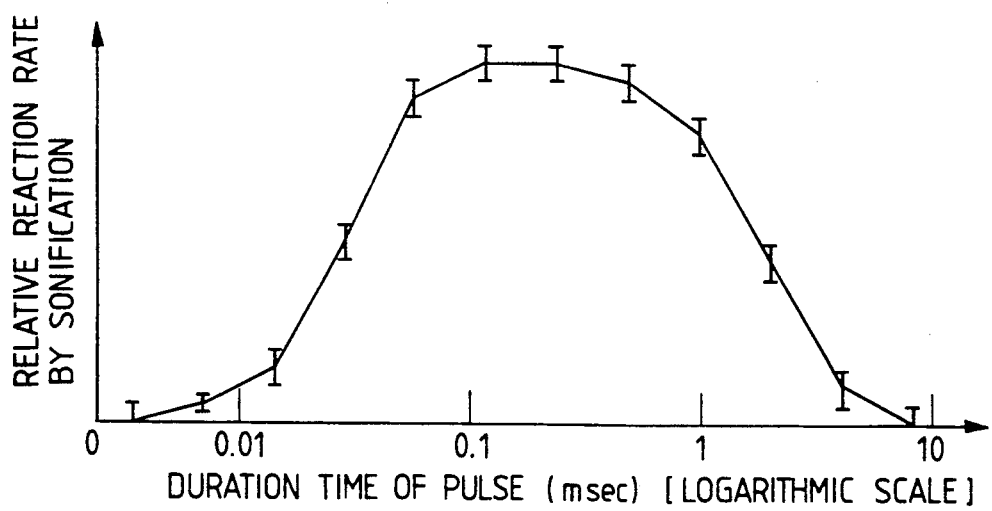
FIG. 7 is a diagram showing the result of measurement of the velocity of the ultrasonic wave chemical reaction by changing a burst wave duration time.

Another important factor for conducting efficiently the acoustic chemical reaction by utilizing the formation and rupture of the cavitation is a time interval in which a plurality of acoustic fields are switched. To examine this factor, the reaction rate is determined from the change of absorbancy by utilizing the color change of an aqueous solution to violet due to iodine precipitated by the chemical reaction caused by the irradiation of the ultrasonic wave in the system prepared by adding starch and carbon tetrachloride to the aqueous potassium iodide solution. The acoustic field of the simple focus shown in FIG. 5(B) is used interruptedly for the sake of simplicity. When one kind of acoustic field is irradiated interruptedly, the reaction rate which is by far higher than that of the continuous irradiation can be obtained, though it may be lower than the case where a plurality of kinds of acoustic fields, that are selected most optimally, are switched. The optimum value of the interruption period corresponds substantially to the optimal value of the switching period of a plurality of kinds of acoustic fields. FIG. 7 shows the experimental result when the experiment is conducted by setting the duration time and rest time in the interrupted irradiation to the 1:1 basis. The abscissa represents the logarithmic scale representation of the burst wave duration time. To accomplish an efficient reaction, the duration time of the burst wave must be from 0.01 msec to 10 msec and preferably, from 0.05 msec to 2 msec.

When the burst wave duration time is below a certain length $T_o$, the reaction speed drops drastically, and the spatial selectivity of reaction can be improved by utilizing this drop. In other words, the transducer is divided into a plurality of segments and the ultrasonic wave is irradiated from the different portions of the transducer so as to form convergent acoustic fields whose focal points and acoustic pressure distributions in the focal zone are substantially the same. Then, the duration time of the irradiation of the ultrasonic wave from one segment of the transducer is switched so that it is shorter than the value $T_o$ described above so that it is sufficiently greater then $T_o$ at the focus but is shorter than $T_o$ at the other positions. In this manner the factors of the spatial selectivity of the reaction can be obtained besides the difference in the density of the ultrasonic wave power.

Figure 8A:
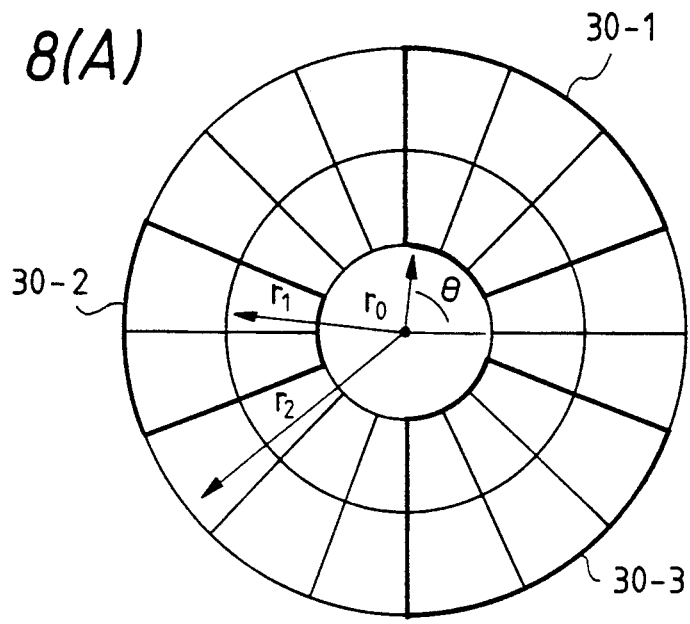
FIGS. 8A and 8B are a bird's-eye view of the intensity distribution of the convergent field formed by a partial transducer and a transmission wave from it.
Figure 8B:
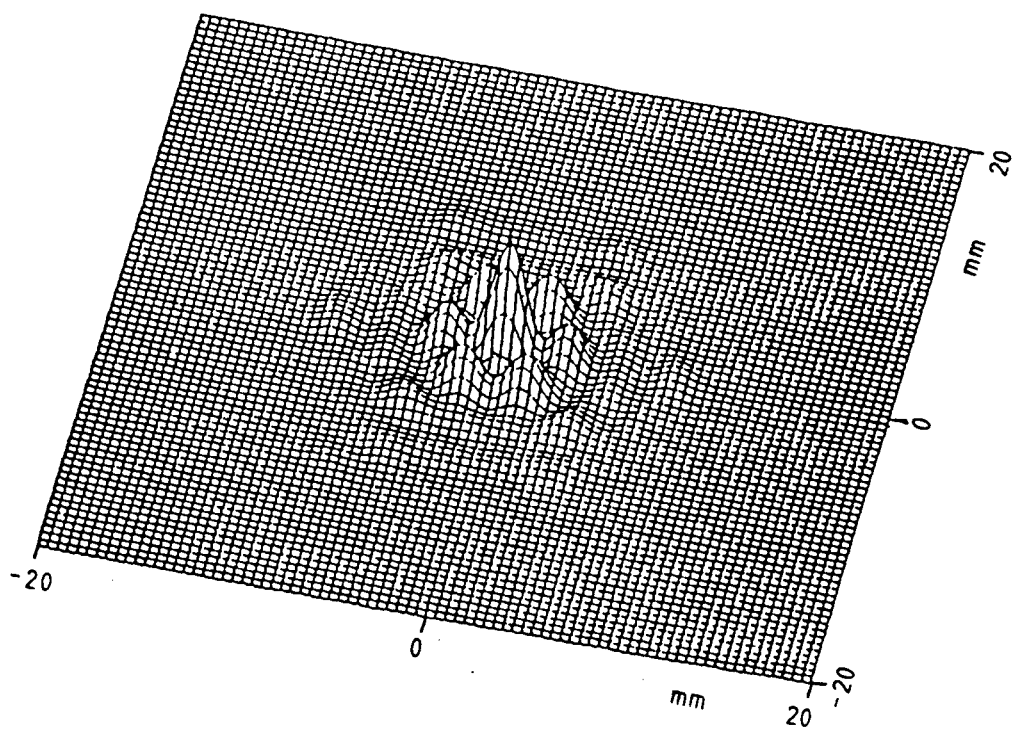

A definite embodiment using the transducer shown in FIG. 2 will be explained with reference to FIG. 8. First of all, the array transducer is divided into segments 30-1, 30-2, 30-3 encompassed by thick lines in the drawing (A) and the rest of portions and when only the segments encompassed by the thick lines are driven and the ultrasonic wave is irradiated, a convergent acoustic field whose concentration distribution is shown in (B) is formed on the focal plane. The segments 30-1, 30-2, 30-3 are selected so that they are complementary with the partial transducer which is point-symmetric with respect to the center of the transducer. Accordingly, the collapse of the beam of the focus due to the partial transducer transmittion can be restricted sufficiently. Next, the partial transducers 30-1, 30-2, 30-3 used for the transmission are rotated around the center of the transducer within the time interval below about $T_o$ described above, or they are used alternately with the complementary partial transducer so that the irradiation duration time becomes shorter than $T_o$ immediately below the transducer. In this case, the beam of the focus at the center of the drawing (B) does not change substantially, and the chemical reaction is allowed to proceed only at this portion.

Figure 5D:
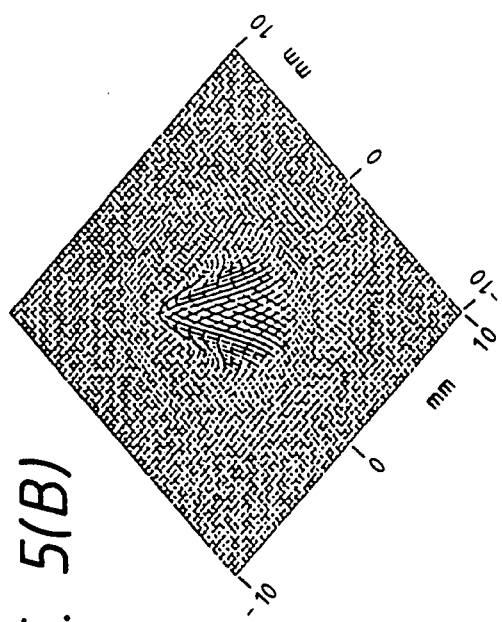

The interior inside the living body is not completely homogeneous acoustically. Therefore, the position of the steady cavitation occurring due to the irradiation of the ultrasonic wave of such an acoustic field is not always acurately at the position of the acoustic pressure minimum point but in some cases, at a deviated position. In the case of the ultrasonic wave irradiation array shown in FIG. 2, the focus can be moved as shown in FIGS. 5C and 5D without forming an unnecessary acoustic field such as a grating lobe of about ±3 mm round the geometric focal plane F. Therefore, even if the stable cavitation somewhat deviates from the center in the drawing, the acoustic pressure maximum point can be formed at the cavitation position itself if that position can be detected by the means described already.

FIGS. 5B, C and D can be regarded as a spatial response function when the transducer for the irradiation is used as a receiving transducer for detecting the cavitation. However, if the ultrasonic wave frequency to be handled is 0.5/n Mhz, the scale of the distance is read n times and when it is 0.5×n MHz, the scale must be read 1/n times. Therefore, when the cavitation is detected by the fractional harmonic components, high location accuracy cannot be expected but scanning can be made over a broad range. On the other hand, when detection is made by a higher harmonic component, high location accuracy can be obtained, though the scannable range is not much broad.

FIG. 9 shows the flowchart of an example of the algorithm for a series of operations such as setting of the irradiation focus, detection of the stable cavitation and change of the irradiation focus. In this example, if the stable cavitation does not occur even when the irradiation continuation time under the same focus condition exceeds a certain predetermined reference value, the gas elution quantity near the acoustic pressure maximum and minimum points is judged insufficient and the irradiation focus condition is changed automatically to move the acoustic pressure maximum and minimum positions. In the example shown in FIG. 5, the acoustic fields A and B are formed by use of the same ultrasonic wave frequency but the frequency of A may be reduced to be relatively lower than that of B. This is directed to generate the cavitation by the ultrasonic wave having a lower frequency which is more effective for the generation of the cavitation and to rupture the cavitation by the ultrasonic wave having a higher frequency which is more likely to concentrate the spatial energy.

Figure 11A:
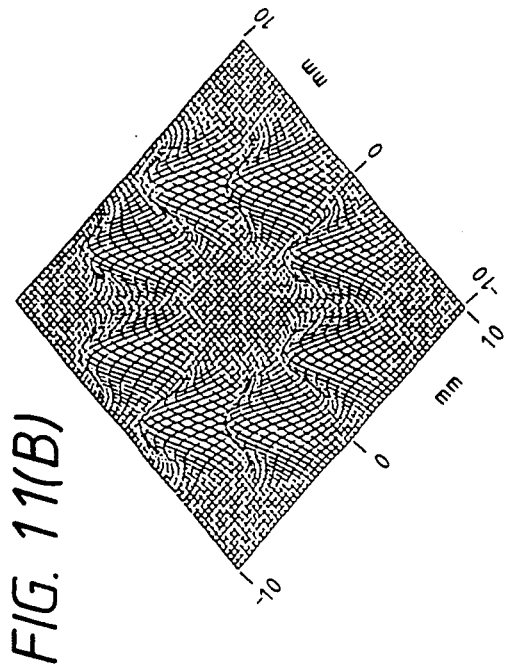
Figure 11B:
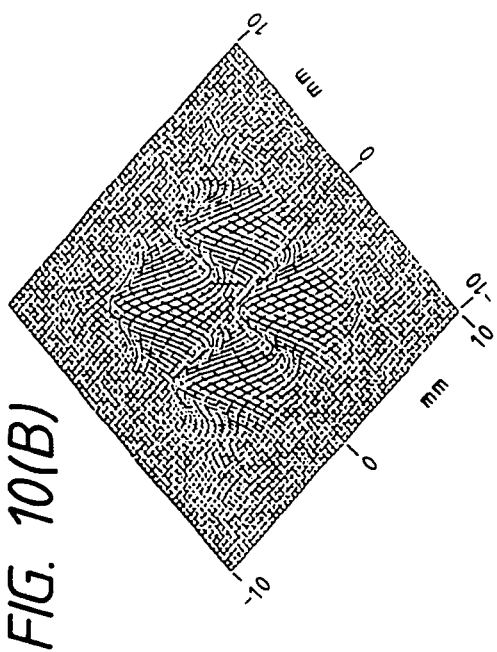
Figure 10A:
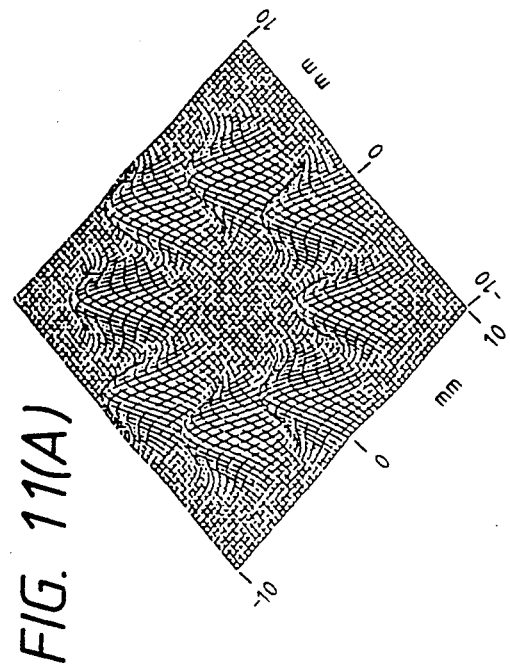
Figure 10B:
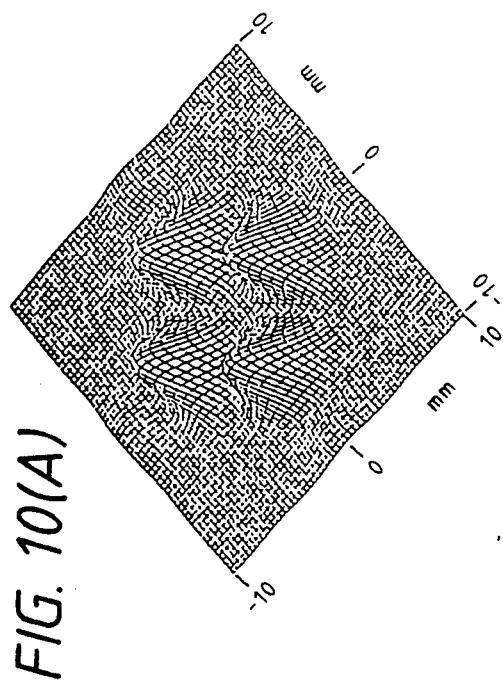

When each element is driven by a signal having an amplitude distribution like a standing wave on the array, such as $$A_i(\theta) = A_o \cos M\theta \exp(-j\omega t) \quad (2)$$

or $$A_i(\theta) = A_o \sin M\theta \exp(-j\omega t) \quad (3),$$

the acoustic field whose intensity distribution is such as one shown in FIGS. 10A, 10B is formed on the geometric focal plane. These drawings show the case where $M=2$, whereby symbol A represents the acoustic field generated by the driving signal of the formula (2) while the symbol B does the acoustic field generated by the driving signal of the formula (3). In both cases, however, each element is driven by the driving signal obtained by approximating the cosine function and sine function in the formulas by the rectangular function. The acoustic pressure maximum point of the acoustic field B is situated at the position of the acoustic pressure minimum point interposed by the acoustic pressure maximum points of the acoustic field A, while the acoustic pressure maximum point of the acoustic field A is situated at the position of the acoustic pressure minimum point interposed by the acoustic pressure maximum points of the acoustic field B, on the contrary. If the ultrasonic wave is irradiated while the acoustic field is being switched from A to B and vice versa with a suitable time interval, the stable cavitation generated by the acoustic field A is ruptured by the acoustic field B while the stable cavitation generated by the acoustic field B is ruptured by the acoustic field A, on the contrary, so that the generation and rupture of the cavitation effective for the drug activation can be conducted efficiently. Similarly, FIGS. 11A and 11B show the intensity distribution of the acoustic fields generated when $M=4$. In comparison with the case of $M=2$, they are a pair of acoustic fields which is more suitable for the drug activation by the irradiation of the ultrasonic wave over a broader range.

Figure 12:
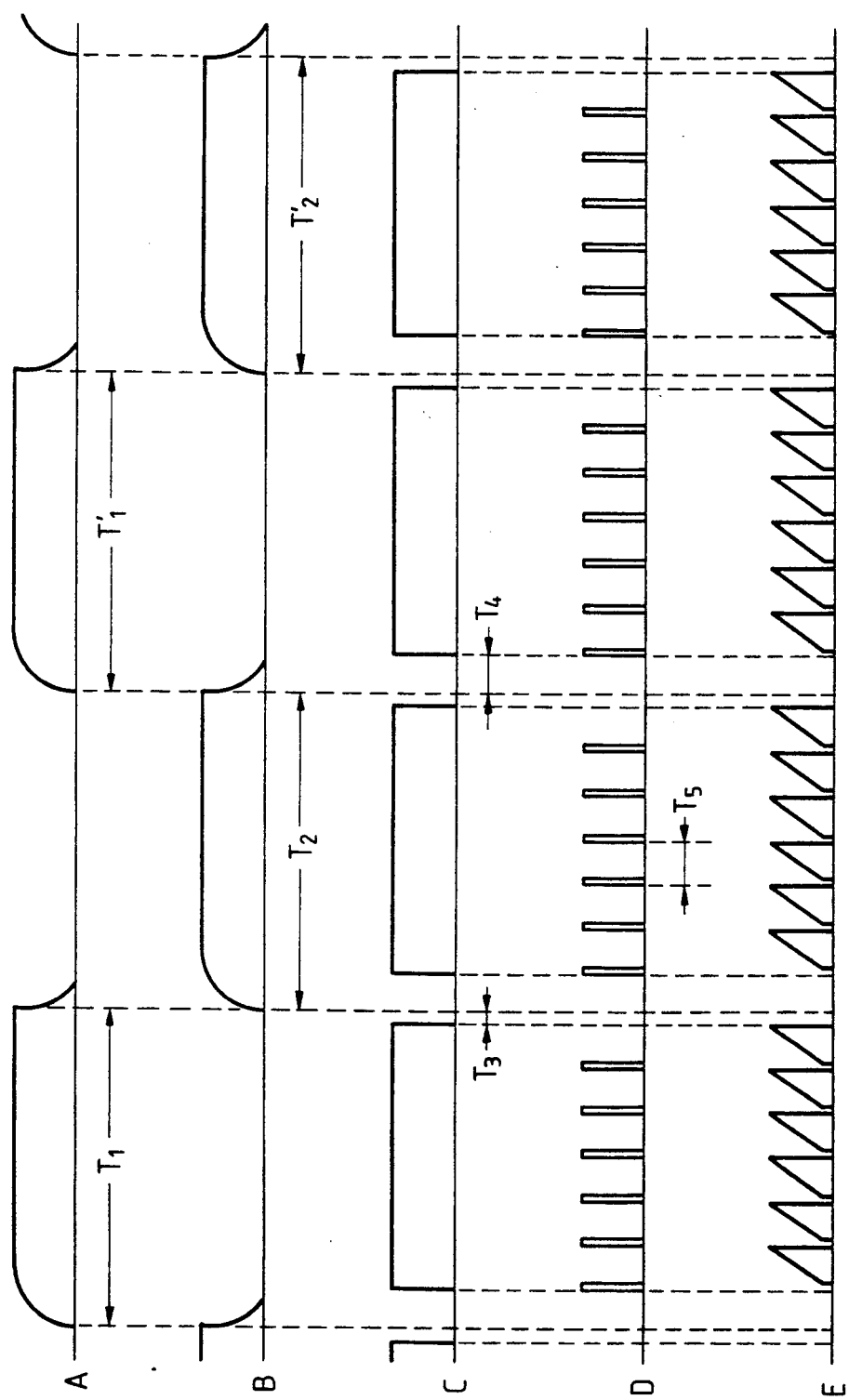

FIG. 12 shows the time chart of the ultrasonic wave irradiation and the cavitation detection in this embodiment. Symbols A and B represent the time chart of the amplitude of the driving signals for generating the two irradiation acoustic fields having the relation such as described above. Irradiation is effected continuously for the periods $T_1$ and $T_2$, respectively, and their switching is made rapidly by electronic control. Symbol C represents the time chart of the gain of each receiving amplifier 5-1-5-N for detecting the cavitation. The gain is lowered to avoid the saturation of the amplifier during the period from before the switching of the irradiation focus $T_3$ to the time $T_4$ after the switching. Symbols D and E represent the amplitude of the transmission driving signal of the probe 4 for imaging and the gain of each receiving amplifier, respectively. In the same way as in an ordinary ultrasonic analytical apparatus, the time interval $T_5$ of the transmission pulse is set to be longer than the time necessary for the ultrasonic wave to reciprocate from the probe to the object region and the gain of the receiving amplifier is controlled as the function of time in accordance with the distance of the echo source. On the other hand, if the probe 4 is used as a passive cavitation detection means for receiving the higher harmonic components emitted from the cavitation, the gain control is conducted in the same way as C. If the mechanism for detecting the generation of the stable cavitation is omitted, the drug activation can be carried out efficiently by selecting suitably the switching time intervals $T_1$ and $T_2$ of the irradiation acoustic fields from within the range of 0.01 msec to 10 msec, as described already.

Though not shown in FIG. 12, an electrocardiograph represented by reference numeral 29 in FIG. 1 is used for a patient having the problem of a cardiac function and switching of the acoustic fields from the first irradiation means to the second irradiation means is conducted in such a manner as to avoid the timing immediately before the contraction period. If the patient has other cardiac problems, the irradiation of the therapeutical ultrasonic wave is stopped for the short period from immediately before till immediately after the contraction period.

FIG. 3 shows the array applicator for irradiating the ultrasonic wave using the rectangular array in accordance with still another embodiment of the present invention. In the drawing, like reference numerals are used to identify those components or portions which have the same functions and the same names as in FIGS. 1 and 2. The rectangular array having major sides of 16 cm and the minor sides of 4 cm is divided into $3 \times N_1$ elements and the elements at both ends of each of the three divided groups are connected electrically with each other. Both irradiation sides of the acoustic matching layer 5 made of an alluminum alloy form a part of a cylindrical surface and an acoustic packing material 8 of a polymer material with a sound speed equal to, or lower than, that of water is packed into the recess. The surface is shaped as a plane or convex so that the applicator forms a geometric focus converting to a line F'-F" as a whole. The major side is divided by $N_1$ while the minor side is divided by 3, too. Therefore, the movement of focus in the direction of depth becomes possible even for the focus on the minor side.

Figure 13A:
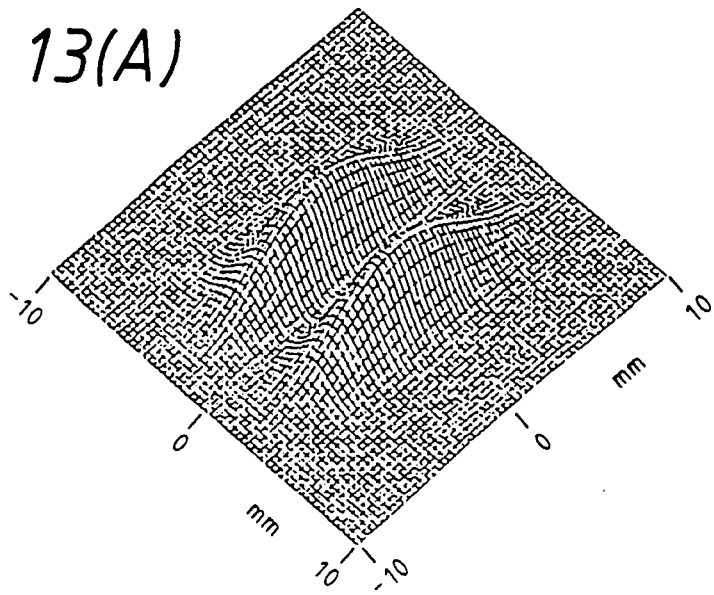
FIGS. 13A, 13B, 14A, 14B, 14C, 14D and 14E are bird's-eye views of the intensity distribution of the field formed on the geometric focus by the ultrasonic applicator of FIGS. 2(A) and 2(B) in the present invention.
Figure 13B:
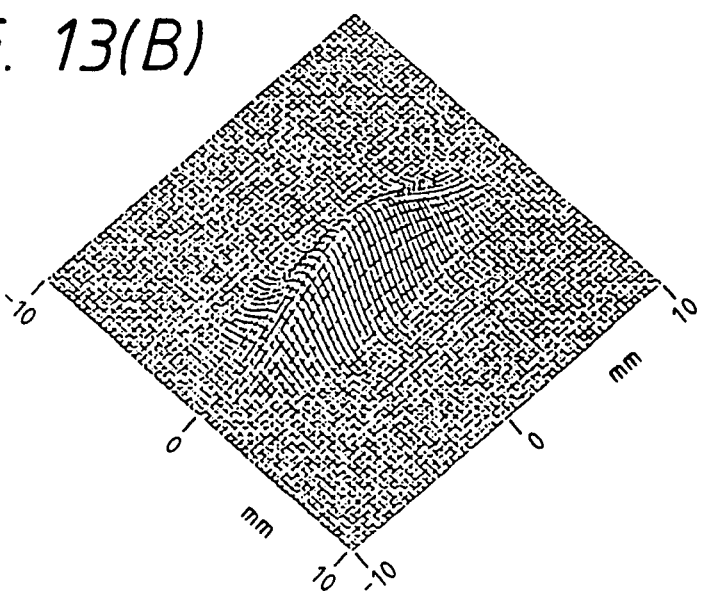
Figure 14A:
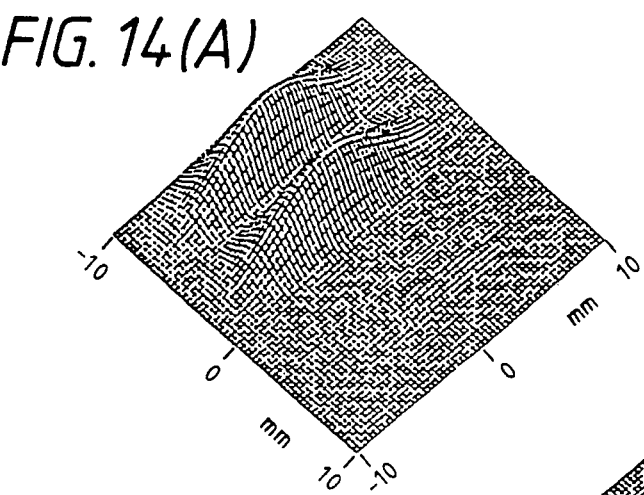
Figure 14D:
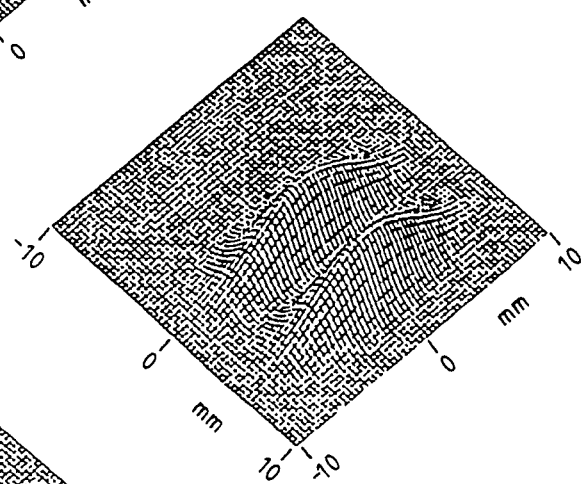
Figure 14B:
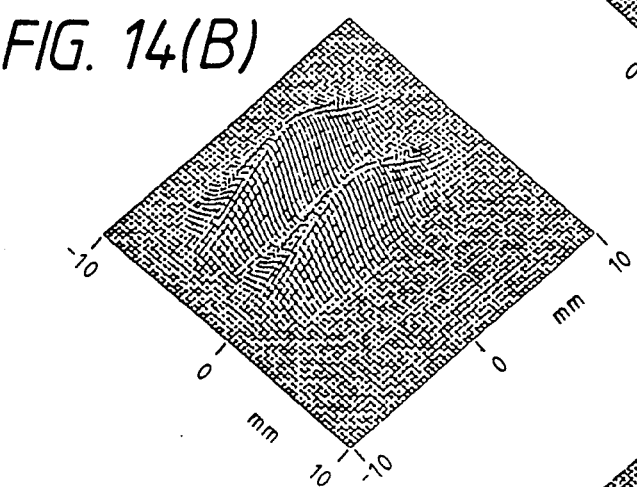
Figure 14E:
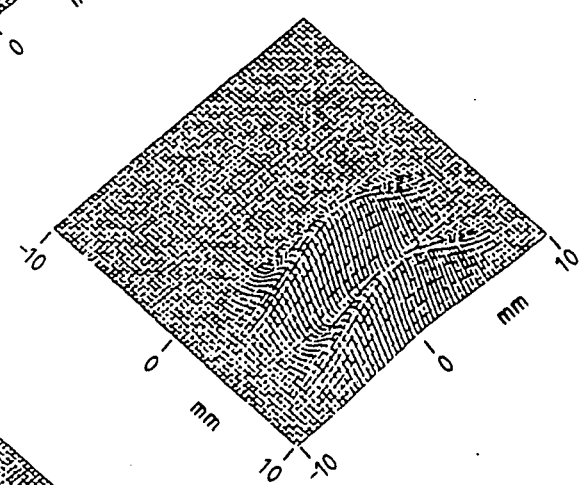
Figure 14C:
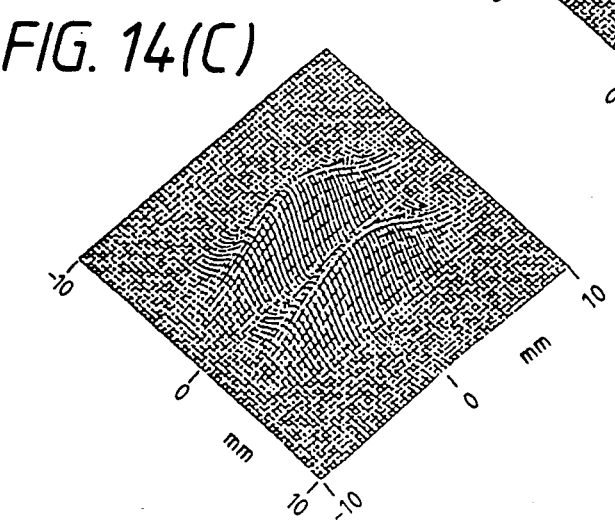

The following will illustrate an example of the acoustic field where a width of 12 cm among the major side of 16 cm is used as an aperture and a ultrasonic wave is irradiated so as to be converged to a position of the distance of 12 cm in front of the aperture. FIG. 13B shows the intensity distribution of the acoustic field formed by an ordinary converging method which drives each element by a signal having a phase difference corresponding to the sound wave propagation time from each element to the focus on the focal plane. In contrast, if the aperature which is 12 cm wide is divided by 6 cm into two segments and each element is driven by a signal whose phase is inversed with respect to one of the divided phases, an acoustic field having an intensity distribution such as shown in FIG. 13A is formed. In the same way as in the embodiment shown in FIG. 5, the acoustic pressure maximum point of the acoustic pressure B is situated at the acoustic pressure minimum point encompassed by the acoustic pressure maximum points of the acoustic field A and the combination of the acoustic fields is suitable so that the stable cavitation generated near the acoustic pressure minimum point generated by the ultrasonic wave irradiation by use of the acoustic field A is ruptured by the acoustic field B. In the same way as in the embodiments shown in FIGS. C and D, the movement of spot focus such as the acoustic field B in the direction of the major side becomes easy by effecting convergence in the direction of the major side or by moving the operture.

FIG. 14 shows an example when the acoustic field generated by the same converging method as the acoustic field A in FIG. 13A is moved in the direction of the major side. There exists the relation between A and B, between B and C, between C and D and between D and E in FIG. 14 such that the acoustic pressure maximum point of one of them is situated at the acoustic pressure minimum point of the other while the acoustic pressure minimum point of one of them is situated at the acoustic pressure maximum point of the other, on the contrary, in the same way as the relation between the acoustic fields A and B of FIGS. 10 and 11. Therefore, if the ultrasonic wave is irradiated by switching the acoustic fields with suitable time interval such as A→B→C→D→E→D→C→B→A, ... , the drug activation can be attained in a broader range.

The drug can be activated by irradiating the ultrasonic wave while switching a plurality of kinds of convergent acoustic fields with the suitable time intervals described above having the superposed focal zones, such as the combination of the acoustic fields (B) and (D) in the drawing, though the acoustic pressure maximum point of one of the fields is not always situated at the zero point of one of them.

Figure 15:
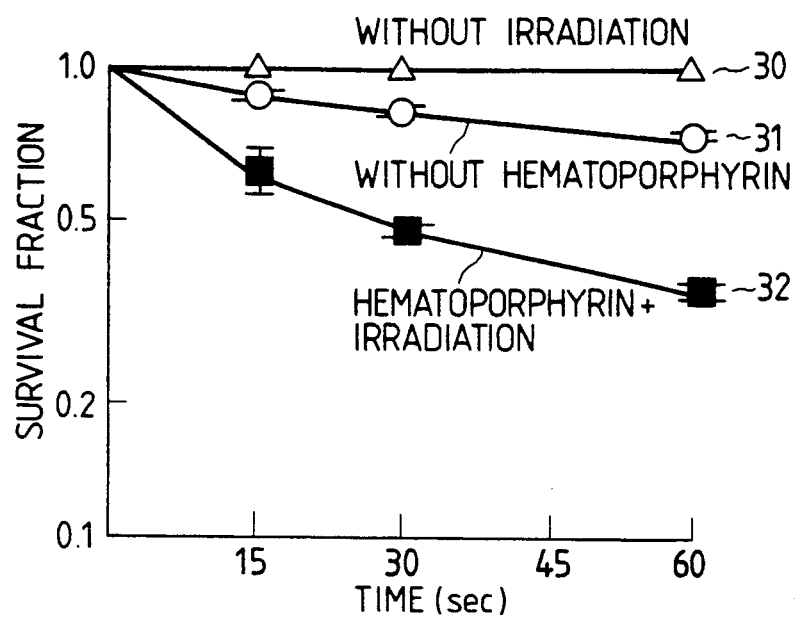

FIG. 15 shows the result of examination of the cell killing effect for tumor cells in a suspension placed into a polyethylene testing tube placed in degassed water by the irradiation of the ultrasonic wave described above. The cells used are sarcoma 180 and the number of surviving cells is determined by counting the number in a predetermined quantity of sample through a microscope. The survival fractions of the tumor cells of a group to which hematoporphyrin is added up to a 5 wt % concentration, a group for which only the ultrasonic wave irradiation is made and a group for which the ultrasonic wave irradiation is made after the addition of hematoporphyrin are represented by numerals 31, 32 and 33 as the function of time, respectively. Hematoporphyrin alone does not at all exhibit the cell killing function and the effect is not great even by the ultrasonic wave irradiation alone, either. When they are combined, however, the number of surviving cells drops to about $\frac{1}{3}$ within 60 seconds and a great cell killing effect can be observed. The appearance of the similar cell killing effect by the irradiation of the ultrasonic wave is also observed in the case of a protoporphyrin. The similar effect can be observed in methylene blue which is similarly a chelating agent, though it is not a prophyrin type compound.

Figure 16:
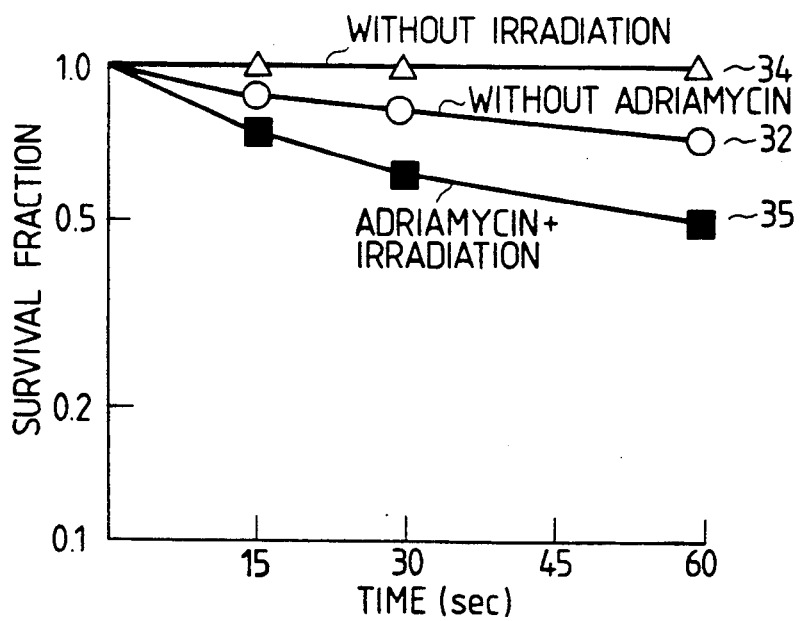
FIGS. 16 and 16 are graphs illustrating drug effects enhanced by ultrasonic irradiation.

Furthermore, the result such as shown in FIG. 16 can be obtained when the same experiment is carried out by use of adriamycin which is an alkylating agent having the similar chelate forming function. This compound provides a remarkable effect of the cell killing effect of the drug by the irradiation of the ultrasonic wave, though it is somewhat lower than that of hematoporphyrin. Adriamycin is known as a compound having by itself the tumor cell killing action but such an action cannot be detected within a short period of 1 minute in this experiment. It can therefore be concluded that the appearance of the cell killing effect of adriamycin by the irradiation of the ultrasonic wave is independent of the tumor cell killing action of the drug alone. This is in common to other alkylating agents such as daunomycin.

Furthermore, the appearance of the same effect can be observed for ascorbic salts which are known as vitamin C, though they have entirely different chemical structures from the compounds described above and their mechanism of killing the tumor cell is believed different, too.

The calculation method of the drug concentration in the body in the system for supporting the cooperation between the drug dose and the ultrasonic wave irradiation in the present invention will be explained about the case where the drug is in advance dosed at a predetermined time before the ultrasonic wave irradiation as described above.

Let's assume that the drug migration constant from the dosed portion into the blood is $k_A$, the elimination rate constant of the drug from the blood is $k_E$, the drug dose is D and the drug and the drug distribution volume is V. If the dose time is $t=0$, then the blood concentration B(t) is given as follows:

$$B(t) = \frac{D}{V} \cdot \frac{k_A}{k_A - k_E} (e^{-k_E t} - e^{-k_A t}) \qquad (4)$$

Here, the blood concentration at the time of dose is set to be $B(0)=0$. In the formula described above, the drug distribution volume V is substantially proportional to the volume of the patient but is affected by the protein combinability of the drug, too. The drug distribution volume V becomes relatively smaller if a patient is greater in length than another, though they have the same volume, because the proportion occupied by the skeletal structure in the weight and volume is generally greater in the former than the latter. In the case of patients having a small quantity of proteins in the blood or in the case of young patients, on the contrary, the drug distribution volume V becomes greater. Therefore, the drug distribution volume V is determined by correcting the volume value on the basis of the information on the patient and the drug name, and the calculation of the formula (4) is made. When the time change of the blood flow rate of the whole body such as the blood flow of the main artery of the abdominal region is measured, the values $k_A$ and $k_E$ are corrected by use of the measured value to make the calculation of the formula (4).

The drug concentration in the tumor C(t) is given by the following formula when the free fractions in the blood and in the tumor are $F_B$ and $F_T$, respectively, and the tumor blood flow rate per unit time and per unit volume is $k_l$:

$$C(t) = \int_0^t B(t-u)k_1 e^{-k_1 u F_T/F_B} du \qquad (5)$$

Here, the drug concentration in the tumor C(0) at the time of dose is set to 0. The quantities of the free fractions $F_B$ and $F_T$ are primarily determined by the drug used but they are also affected by the protein concentration in the blood of the patient, the organ and portion of the organ in which the tumor exists, and whether the tumor is primary or metastatic. Therefore, the values are corrected and used on the basis of the information inputted from the keyboard. When the number of blood vessels flowing into and out from the tumor as the object of therapy is not much great and the blood flow rate can be measured by the Doppler signal processing of the ultrasonic echo signal or the like, $k_l$ can be determined more accurately. When the change of the flow rate of the more whole body can be measured in place of the flow rate flowing into and out from the tumor, such a processing is effective as the information for correcting $k_l$. When the formula (5) is derived, the effect that the drug concentration drops as the dosed drug changes to other substances due to the irradiation of the ultrasonic wave and the change of the blood vessel systems of the tumor due to the effects of the irradiation of the ultrasonic wave and the dosed drug are neglected.

The drug concentration in the tissues other than in the tumor can be calculated by use of a formula similar to the formula (5). Therefore, the drug concentration is calculated and displayed as the function of time for the portions around the tumor subjected to the ultrasonic wave irradiation in order to assist the therapy having higher safety.

The "pharmacokinetical ultrasonic dose" Du(t), which is defined by the following formula by use of the ultrasonic wave irradiation intensity I(t) and the drug concentration in the tumor C(t) determined from the formula (5), is calculated and displayed every moment, and its final value is recorded for the future diagnosis and therapy of the patient:

$$Du(t) = \int t_0 \, G(I(t)) \cdot H(C(t)) dt \qquad (6)$$

Here, symbols G and H are those functions which convert the ultrasonic wave irradiation intensity and the drug concentration in the tumor to the effective intensity and to the effective concentration, respectively. The effects of both the ultrasonic wave irradiation intensity and the drug concentration in the tumor appear when they exceed certain threshold values, respectively, and their effects get into saturation when they exceed certain greater threshold values, respectively. Therefore, a quantitative scale can be obtained by correcting and converting these values.

As described above, if the drug of the present invention is dosed to the patient and the acoustic field for generating and rupturing selectively and efficiently the cavitation at the object region by use of the ultrasound irradiation apparatus of the invention in good cooperation by utilizing the therapeutical schedule support system of the invention, the anticancer activation of the drug can be attained locally at the object region and the cancer therapy can be accomplished with a reduced side effect.

In the description of the foregoing embodiments, the embodiments using the two kinds of array type ultrasonic wave applicators have been described particularly in detail but the present invention is not limited thereto. For example, though the foregoing description of the ultrasonic wave applicator explains the case where a plurality of kinds of convergent acoustic fields for generating and rupturing the cavitation are formed by the same transducer and the foci of the convergent acoustic fields are scanned electronically, the application range of the present invention includes the case where independent electro-acoustic transducers are used for generating a plurality of kinds of convergent acoustic fields and the case where the focuses of the convergent acoustic fields are scanned mechanically.

Though the foregoing description explains in detail the application of the drug activation by the ultrasonic wave irradiation for the cancer therapy, the application range of the present invention is not limited thereto but includes also the litholytical therapy by the application of the drug activation by the ultrasonic wave irradiation and the synthetic chemical industry and biochemical industry.

What is claimed is:

1. An ultrasonic apparatus for therapeutical use by locally activating an anti-tumor effect of a drug injected into a living body, the apparatus including:
   means for irradiating the living body with a plurality of converged ultrasonic waves having different focal positions of different acoustic pressure distribution shapes so as to provide a mutually overlapping focal zone at which the anti-tumor effect of the drug is to be activated; and
   means for switching respective irradiations of the plurality of converged ultrasonic waves and enabling irradiation of a respective one of the plurality of converged ultrasonic waves for a switching time between 0.01 msec and 10 msec so as to activate the anti-tumor effect of the drug.

2. An ultrasonic apparatus for therapeutical use by locally activating an anti-tumor effect of a drug injected into a living body, the apparatus comprising:
   transducer means including a plurality of elements for irradiating the living body with a plurality of converged ultrasonic waves having mutually different acoustic pressure shapes and different focal positions with a mutually overlapping focal zone at which the anti-tumor effect of the drug is to be activated;
   means for sequentially driving predetermined ones of the elements of the transducer means so that a respective one of the plurality of converged ultrasonic waves has a driving time between 0.01 msec and 10 msec to enable activation of the anti-tumor effect of the drug.

3. An ultrasonic apparatus for therapeutical use according to claim 2, wherein the driving means further includes means for driving the transducer means so as to provide a driving time shorter than 0.1 msec for at least one of the plurality of converged ultrasonic waves.

* * * * *